Figure 1:
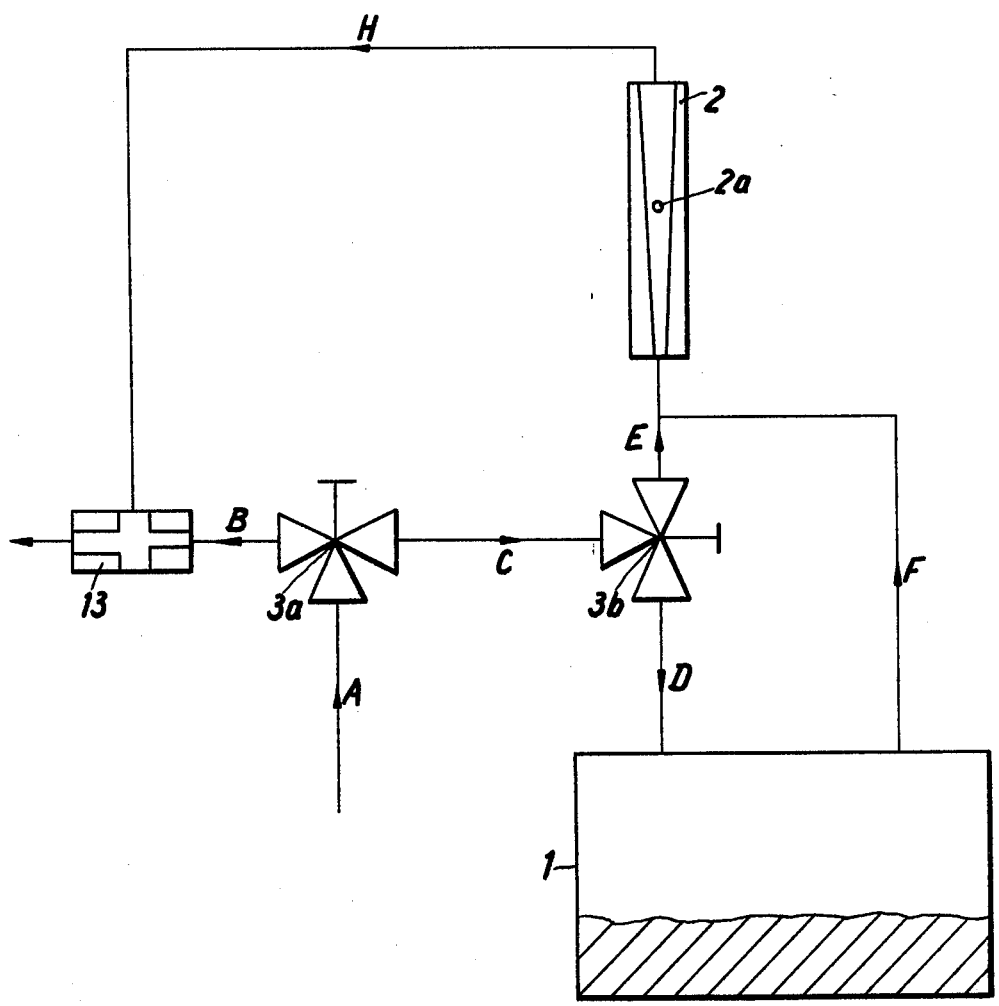

United States Patent [19]

Hamalainen et al.

[11] 4,091,056
[45] May 23, 1978

[54] METHOD OF VAPORIZING LIQUIDS

[76] Inventors: Veikko Hamalainen, Vaahtorinne 3 C 38, 01600 Myyrmaki, 00910 Helsinki; Jaakko Aarnio, Haarniskatie 6 B 13, 00910 Helsinki, both of Finland

[21] Appl. No.: 568,153

[22] Filed: Apr. 15, 1975

Related U.S. Application Data

[62] Division of Ser. No. 372,623, Jun. 22, 1973, Pat. No. 3,941,861.

[30] Foreign Application Priority Data

Jun. 28, 1972  Finland ................................. 721827
Sep. 11, 1972  Finland ................................. 722494
Feb. 22, 1973  Finland ................................. 73545

[51] Int. Cl.² .............................................. B01F 3/04
[52] U.S. Cl. ........................................ 261/19; 73/1 R; 73/3; 73/194 R; 128/188; 261/64 R; 261/75; 261/119 R; 261/DIG. 65
[58] Field of Search ............... 261/DIG. 65, DIG. 34, 261/19, 35, 64 R, 76, 142, 135, 128, DIG. 17, 129, 130, 75, 119 R; 128/188, 194, 185, 186, 192, 193; 73/1 R, 3, 194 R; 122/232-234, DIG. 1, DIG. 2, DIG. 7

[56] References Cited

U.S. PATENT DOCUMENTS

| 1,925,002 | 8/1933 | Reeder | 261/76 X |
| 1,930,848 | 10/1933 | Ashley et al. | 261/DIG. 17 |
| 2,212,598 | 8/1940 | Hagist | 261/76 |
| 2,870,764 | 1/1959 | Carlson et al. | 128/188 |
| 3,128,764 | 4/1964 | Koehn | 128/188 |
| 3,166,676 | 1/1965 | Robinson | 128/188 |
| 3,171,411 | 3/1965 | Levine | 128/188 |
| 3,251,361 | 5/1966 | Rusz | 128/188 |
| 3,313,298 | 4/1967 | Schreiber | 128/188 |
| 3,527,213 | 9/1970 | Schreiber | 261/35 X |
| 3,528,418 | 9/1970 | Grosholz et al. | 261/DIG. 65 |
| 3,532,270 | 10/1970 | Schoen, Jr. | 261/DIG. 34 |

*Primary Examiner*—Tim R. Miles
*Assistant Examiner*—Richard L. Chiesa
*Attorney, Agent, or Firm*—Burnes, Doane, Swecker & Mathis

[57] ABSTRACT

An apparatus is disclosed for delivering a controlled and metered amount of vapors of a vaporizable liquid in a carrier gas to a destination for use there (e.g., ether vapors to a mask for use in anesthesia during surgery). A feature of the apparatus is a metering device in which the height of a ball floating in the gas stream indicates the rate of flow.

2 Claims, 5 Drawing Figures

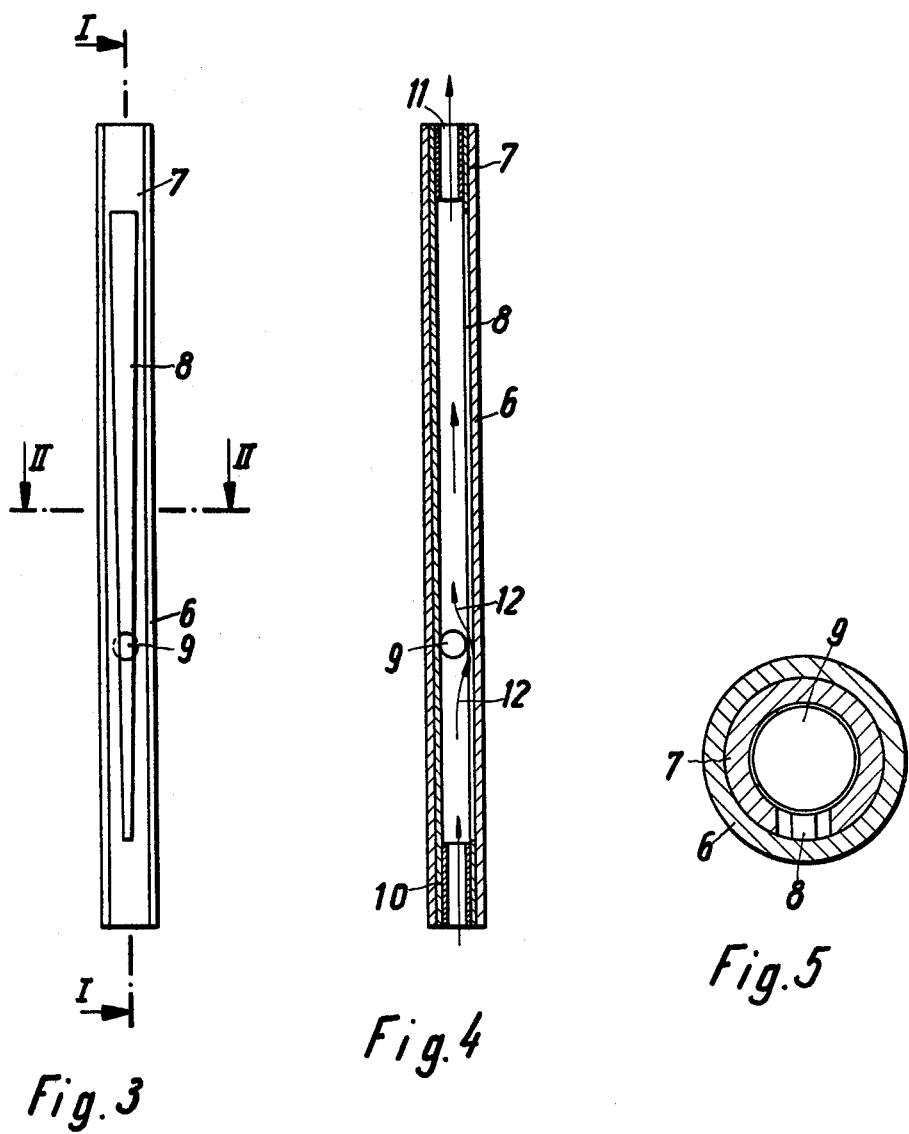

METHOD OF VAPORIZING LIQUIDS

This is a division of application Ser. No. 372,623, filed June 22, 1973, now U.S. Pat. No. 3,941,861.

This invention relates to a vaporizing apparatus for liquids which preferably evaporate at room temperature. Prior art vaporizing apparatuses used in medicine, for instance for dosing liquid anesthetic such as ether to a patient, have drawbacks in that the amount of vaporized ether cannot be directly measured and thus not visually controlled during the procedure.

The aim of this invention is to eliminate the said drawbacks by means of an apparatus in which the total gas flow is led to a three-way valve from where one way leads one part of the gas to an ejector which causes suction downstream of a metering device and the other part of the gas flows to another three-way valve which divides the gas further into two parts of desired proportion so that one part flows directly to the metering device, and the other part flows through a vaporizing vessel to the metering device. The metering device is calibrated so that it indicates a desired gas flow already in zero position. Thus the gas flow passing through the vaporizing vessel is saturated by vapour which causes an increase in the indication of the metering device and this increase represents the proportion of the vapour in the total flow.

The above aims are achieved by an apparatus according to the invention, the characteristics of which are set forth in the claims.

Figure 2:
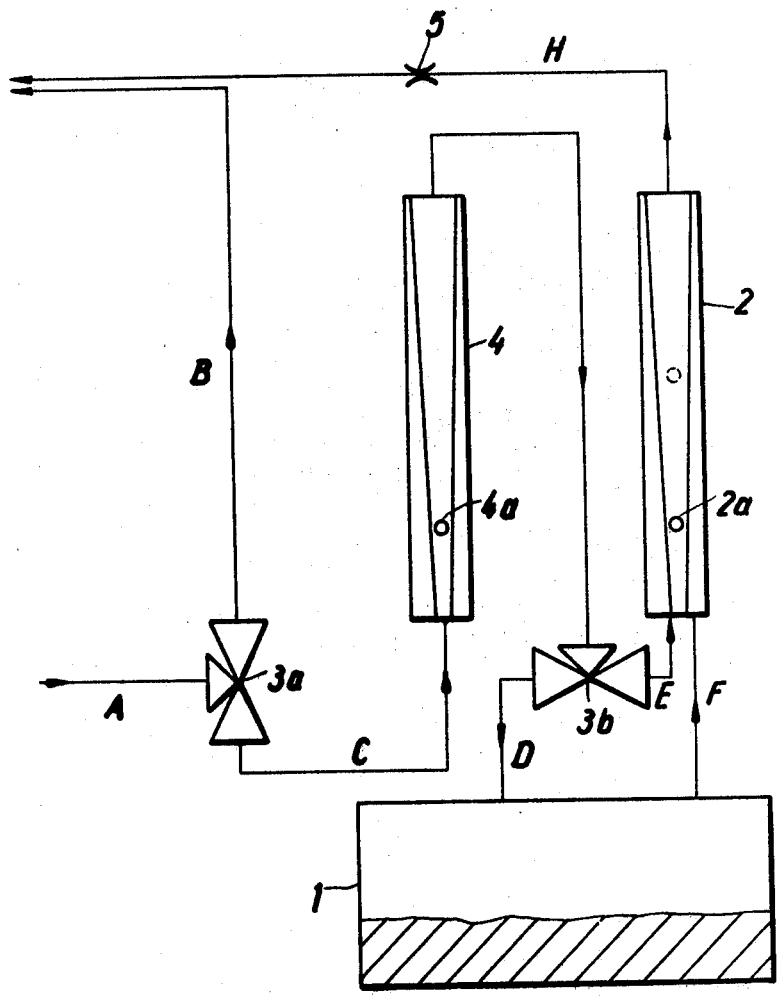

Preferred embodiments of the invention will now be described with reference to the accompanying drawings in which:

FIG. 1 shows schematically one embodiment of a vaporizing apparatus according to the invention, FIG. 2 shows schematically another embodiment of a vaporizing apparatus according to the invention, FIG. 3 shows a front view of a flow meter belonging to a vaporizing apparatus according to the invention, FIG. 4 shows a section of the flow meter of FIG. 3, taken on line I—I, and FIG. 5 shows an enlargened top view of the flow meter of FIG. 3 in section taken on line II—II of FIG. 3.

The capital letters refer to gas flows.

As shown in FIG. 1, the total gas flow A is lead to a three-way valve 3a, where it is divided into two parts, B and C. Part C is led to a three-way valve 3b, which has an initial position where C=E; this situation represents the zero position of a metering device 2. When vapour is needed, flow D is adjusted by the valve 3b so that a desired amount of vapour is carried by the gas flow. The greatest amount of vapour is carried when C=D, E=O and F + vapour = H. The position of a ball 2a of the metering device indicates the proportion of vapour in the gas flow. The construction of the metering device 2 is such that the ball in it already in zero position represents a certain gas flow. The purpose of an ejector 13, where gas flow B is led to, is to assist in vaporizing the liquid by causing underpressure downstream of the metering device 2.

In FIG. 2, a controlling meter 4 is arranged in the vaporizing apparatus before the three-way valve 3b, in order to measure gas flow C. One feature of the invention is the changeability of the scales of the two flow meters so that the vaporizing apparatus can be used for vaporizing several different liquids, i.e., the use of the apparatus is not restricted to vaporizing only a certain liquid. According to the invention, it is preferable to use also a throttle 5 in the gas flow after the second flow meter 2. In this way the meter is steady and easier to read.

As shown in FIG. 2, the total gas flow A is led to the three-way valve 3a where it is divided into two parts: gas flow B and gas flow C. According to the invention, gas flow C is led through the metering device 4 to the three-way valve 3b. The metering device 4 may be similar to the metering device 2. The controlling flow meter 4 is preferably made so that it is at least partly transparent. The ball 4a of the metering device 4 indicates the rate of gas flow C. In the three-way valve 3b gas flow C is divided into flows E and D in desired proportion. Gas flow E is led directly to the metering device 2 and gas flow D is led to the metering device 2 through the vaporizing vessel 1. Flow F coming from the vaporizing vessel 1 to the metering device 2 includes, besides gas flow D, also vapour from the vaporizing vessel 1. Gas flow H after the metering device 2 is throttled at point 5 in a suitable way so that the positions of the balls 2a and 4a of the metering devices are as steady as possible.

In this way, the metering devices 2 and 4 are easier to read. The metering devices 2 and 4 are preferably provided with changeable scales, each liquid to be vaporized having its own scale. In this way the use of the vaporizing apparatus is not restricted only to vaporizing one certain liquid, and it can be used for vaporizing several various liquids while it is always possible to observe the proportion of each vapour in the total gas flow.

A flow meter 2, 4 belonging to an apparatus according to the invention will be described in the following, with reference to FIGS. 3 to 5.

The flow meter in question can be used for measuring gas and liquid flows in a whole desired range of flow variations or only in a part of the range, i.e., above a certain flow value.

The flow meter comprises two tubes 6 and 7, the tube 7 being wihin the tube 6. The outer tube 6 is made of transparent material, preferably glass or plastic. The material of the inner tube 7 is metal, glass or plastic, for instance. According to the invention, the inner tube 7 has a longitudinal groove or slot 8, going through the wall of the tube 7 and widening upwards when the meter is in operating position. The sides of the slot 8 are preferably machined straight so that the groove or slot 8 widens evenly from the bottom to the top. According to the invention, the tube 7 can be provided also with several grooves or slots 8, for instance with two slots 8, on opposite sides of tube 7 so that one can see through the meter.

A ball 9 is arranged inside the tube 7 of the meter so that the ball can move freely in the longitudinal direction of the tube 7. The path of movement of the ball 9 is restricted at its ends by suitable stoppers 10 and 11, made of tube, for instance, so that the length of the path is substantially equal to the length of the groove or slot 8. It should be noted that the inner diameter of the inner tube 7 is the same along the entire length of the tube differently from prior art meter constructions.

When a gas or liquid flow is led through a flow meter according to the invention, the flow meter is in vertical position, as shown in FIGS. 3 and 4, so that the wider end of the groove or slot 8 is pointing upwards. A gas or liquid flow passing from below upwards in the tube 7 passes in the way shown by arrows 12 in FIG. 4, i.e., it passes the ball 9 along the slot 8 or alternatively several slots 8. If the gas or liquid flow increases, it pushes the ball 9 upwards in the tube 7 so that the transverse area of the slot or slots 8 at the position of the ball 9 corresponds to the flow. If the gas or liquid flow decreases, the ball 9 sinks correspondingly in the tube 7. Thus the position of the ball 9 indicates the rate of flow through the meter. The meter is provided with a scale at a suitable location, for instance on the surface of the inner tube 7, on the sides of the slot 8, so that the rate of flow can be read directly on the scale from the position of the ball 9.

The accuracy of the flow meter depends on the thickness of the wall of the inner tube 7 and on the increase in width per length of the slot, among other things. By means of the above variables it is possible to define what length of the scale, i.e. what movement of the ball 9 corresponds to a certain volume flow through the meter. Thus a scale of desired length and also of required accuracy can be made for instance for volume flow variations from 0 to 2 liters per minute.

The flow meter can also be made so that it shows the rate of flow only starting from a certain value of the rate of flow. In this case the ball 9 of the flow meter stays in its lower position on flow rates smaller than the flow rate in question, because the lower end of the slot 8 has been made to correspond to the flow rate in question. The gas or liquid flow can pass the ball 9 in its lower position freely through the slot 8 until the flow increases to a certain value. Only when the rate of the volume flow further increases after this, the ball 9 rises in the tube 7 and indicates the rate of volume flow passing through the meter. The movement of the ball 9 in the meter is even, at least when only one slot 8 is used, because the ball 9 then rolls evenly in the tube 7 along the wall opposite to the slot 8. But even with several slots 8, the ball 9 cannot move unevenly to any noticeable degree because the inner diameter of the tube 7 is the same along the entire length of the tube 7 and the diameter of the ball 9 can be chosen to be nearly the same as the inner diameter of the tube 7.

The invention is not, of course, limited to the above embodiments, and it can vary considerably in details within the scope of the claims.

We claim:

1. A method for delivering a controlled and predetermined amount of vapors of a vaporizable liquid to a destination for use there which comprises:
   (a) providing a stream of carrier gas;
   (b) dividing said stream into two substreams;
   (c) directing a first of said substreams to a suction zone;
   (d) passing the second of said substreams through a first gasflow metering zone to produce a metered substream of carrier gas;
   (e) further dividing said metered substream of carrier gas into two portions of predetermined and controllably variable amounts;
   (f) directing a first of said portions to a second gas-flow metering zone;
   (g) passing the second of said portions through a body of vaporizable liquid to vaporize said liquid and produce a first mixed stream of vapor and carrier gas while regulating the relative amounts of carrier gas in said first and second portions to obtain the desired amount of vapor in said mixed stream;
   (h) passing said first mixed stream of vapor and carrier gas through said second gas-flow metering zone to produce a second mixed stream comprising vapor and said first and second portions of carrier gas;
   (i) passing said second mixed stream of vapor and carrier gas through said suction zone; and
   (j) passing said second mixed stream of vapor and carrier gas from said suction zone to said destination for use.

2. A method according to claim 1 further comprising calibrating the second gas-flow metering zone to indicate zero flow when none of the second portion of metered substream of carrier gas passes through the body of vaporizable liquid, whereby said second gas-flow metering zone will indicate only the amount of vaporized liquid-containing gas flowing to the destination when a controlled amount of said second portion of metered substream of carrier gas flows through said body of vaporizable liquid.

* * * * *